United States Patent
Yurgelun-Todd et al.

(10) Patent No.: US 8,524,665 B2
(45) Date of Patent: Sep. 3, 2013

(54) USE OF SECRETIN IN TREATMENTS OF DISORDERS ASSOCIATED WITH THE AMYGDALA

(75) Inventors: Deborah A. Yurgelun-Todd, Bedford, MA (US); Perry F. Renshaw, Bedford, MA (US)

(73) Assignee: The McLean Hospital Corporation, Belmont, MA (US)

(*) Notice: Subject to any disclaimer, the term of this patent is extended or adjusted under 35 U.S.C. 154(b) by 1584 days.

(21) Appl. No.: 10/556,134

(22) PCT Filed: May 13, 2004

(86) PCT No.: PCT/US2004/015282
§ 371 (c)(1),
(2), (4) Date: Feb. 12, 2007

(87) PCT Pub. No.: WO2004/100899
PCT Pub. Date: Nov. 25, 2004

(65) Prior Publication Data
US 2007/0185018 A1    Aug. 9, 2007

Related U.S. Application Data

(60) Provisional application No. 60/470,177, filed on May 13, 2003.

(51) Int. Cl.
| A61K 38/22 | (2006.01) |
| A61K 31/00 | (2006.01) |
| A61K 38/00 | (2006.01) |
| A61P 25/18 | (2006.01) |
| A61P 25/00 | (2006.01) |
| A61P 25/24 | (2006.01) |
| C07D 211/00 | (2006.01) |
| C07D 307/00 | (2006.01) |

(52) U.S. Cl.
USPC ............. 514/12.8; 514/1; 514/1.1; 514/9.7; 514/17.5; 514/17.6; 546/186; 549/469

(58) Field of Classification Search
None
See application file for complete search history.

(56) References Cited

U.S. PATENT DOCUMENTS 4,443,469 A * 4/1984 Nishizono .................. 514/431
5,585,118 A    12/1996 Stoll (Continued)

FOREIGN PATENT DOCUMENTS

| WO | WO01/32196 | 5/2001 |
| WO | WO01/37801 | 5/2001 |
| WO | WO03/042654 A2 | 5/2003 |
| WO | WO03/092716 | 11/2003 |

OTHER PUBLICATIONS

Williams KJ, Wray JJ, and Wheeler DM, "Intravenous secretin for autism spectrum disorder", Cochrane Database of Systematic Reviews, 2009, Issue 2, pp. 1-50.*

(Continued)

*Primary Examiner* — Chris R Tate
*Assistant Examiner* — Aaron J Kosar
(74) *Attorney, Agent, or Firm* — Clark & Elbing LLP

(57) ABSTRACT

In general, the present invention provides methods for treating disorders associated with the amygdala. The methods of treatment are based on the administration of a therapeutically effective amount of secretin to an individual suffering from a disorder associated with the amygdala, e.g., bipolar disorder or a substance use disorder.

5 Claims, 3 Drawing Sheets fMRI Pre/Post Conditions:
Affect Discrimination Task

(56) References Cited

U.S. PATENT DOCUMENTS

| | | | |
|---|---|---|---|
| 5,693,608 | A | 12/1997 | Bechgaard et al. |
| 6,020,310 | A | 2/2000 | Beck et al. |
| 6,020,314 | A | 2/2000 | McMichael |
| 6,117,890 | A | 9/2000 | Bymaster et al. |
| 6,197,746 | B1 | 3/2001 | Beck et al. |
| 6,498,143 | B1* | 12/2002 | Beck et al. ............ 514/9.7 |
| 6,790,825 | B2* | 9/2004 | Beck et al. ............ 514/9.7 |
| 7,091,182 | B2* | 8/2006 | Beck et al. ............ 514/9.7 |
| 2002/0019364 | A1* | 2/2002 | Renshaw ............ 514/46 |
| 2003/0096264 | A1 | 5/2003 | Altar et al. |
| 2004/0146495 | A1* | 7/2004 | Beck et al. ............ 424/94.3 |
| 2005/0002922 | A1* | 1/2005 | Boismenu et al. ............ 424/94.2 |
| 2006/0035889 | A1* | 2/2006 | Tedford et al. ............ 514/220 |
| 2007/0072233 | A1* | 3/2007 | Levitt et al. ............ 435/6 |
| 2009/0088404 | A1* | 4/2009 | Freedman et al. ............ 514/46 |
| 2009/0104171 | A1* | 4/2009 | Pardee et al. ............ 424/94.1 |

OTHER PUBLICATIONS

Lam, I.P.Y. et al "Multiple Actions of Secretin in the Human Body" International Review of Cytology, 2008, vol. 265, pp. 159-190.(Abstract Only).*

Herlihy, W.C. "Repligen Reports Initial Clinical Data for Secretin in Schizophrenia" RepliGen Corporation Press Release, Feb. 4, 2005, 2 pages.*

Herlihy, W.C. "Repligen Licenses Patent Rights for Treatment of Bipolar Disorder", RepliGen Corporation Press Release, Mar. 31, 2009, 2 pages.*

Ford, N. "The Use of Anticonvulsants in Posttraumatic Stress Disorder: Case Study and Overview" J. Traumatic Stress, 1996, 9(4),, pp. 857-863.*

Horvath et al. "Gastrointestinal abnormalities in children with autistic disorder" Journal of Pediatrics 1999, 135:559-563.

Adolphs et al. "The Human Amygdala in Social Judgement" Nature 393:470-474. (1998).

Adolphs et al. "Abnormal Processing of Social Information from Faces in Autism" J. Cog. Neurosci. 13:232-240. (2001).

Adolphs et al. "Impaired Recognition of Emotion in Facial Expressions Following Bilateral Damage to the Human Amygdala" Nature 372:669-672. (1994).

Adolphs et al. "Fear and the Human Amygdala" J. Neurosci. 15:5879-5891. (1995).

Baird et al. "Functional Magnetic Resonance Imaging of Facial Affect Recognition in Children and Adolescents" J. Am. Acad. Child. Adolesc. Psychiatry 38:195-199. (1999).

Baron-Cohen et al. "The Amygdala Theory of Autism" Neurosci. Biobehav. Rev. 24:355-364. (2000).

Baron-Cohen et al. "Social Intelligence in the Normal and Autistic Brain: An fMRI Study" Eur. J. Neurosci. 11:1891-1898. (1999).

Breiter and Rauch "Functional MRI and the Study of OCD: From Symptom Provocation to Cognitive-Behavioral Probes of Cortico-Striatal Systems and the Amygdala" Neuroimage 4:S127-S138. (1996).

Coniglio et al. "A Randomized, Double-Blind Placebo-Controlled Trial of Single-Dose Intravenous Secretin as Treatment for Children With Autism" J. Pediatr. 138:649-655. (2001).

Davis. "Neurobiology of Fear Responses: the Role of the Amygdala" J. Neuropsychiatry Clin. Neurosci. 9:382-402. (1997).

Emery and Amaral. "The Role of the Amygdala in Primate Social Cognition" Chapter 8 in: Cognitive Neuroscience of Emotion (Lane RD, Nadel L, eds), pp. 156-191. New York. (2000).

Goulet et al. "A Secretin I.V. Infusion Activates Gene Expression in the Central Amygdala of Rats" Neuroscience 118:881-888. (2003).

Hariri et al. "Dextroamphetamine Modulates the Response of the Human Amygdala" Neuropsychopharmacology 27:1036-1040. (2002).

Hariri. "Modulating Emotional Responses: Effects of a Neocortical Network on the Limbic System" NeuroReport 11:43-48. (2000).

Herlihy et al., "Age and Number of Doses are Determinants of the Response to Secretin in Young Children with Autism" International Meeting for Autism Research (IMFAR). Orlando, FL. (2002).

Horvath et al. "Improved Social and Language Skills After Secretin Administration in Patients with Autistic Spectrum Disorders" J. Assoc. Acad. Minor. Phys. 9:9-15. (1998).

Howard et al. "Convergent Neuroantomical and Behavioural Evidence of an Amygdala Hypothesis of Autism" NeuroReport 11:2931-2935. (2000).

Kalin et al. "Functional Magnetic Resonance Imaging Studies of Emotional Processing in Normal and Depressed Patients: Effects of Venlafaxine" J. Clin. Psychiatry 58:32-39. (1997).

Kosaka et al. "Differential Amygdala Response During Facial Recognition in Patients With Schizophrenia: An fMRI Study" Schizophr. Res. 57:87-95. (2002).

LeDoux. "Emotional Networks and Motor Control: A Fearful View" In Prog. Brain Res. 107:437-446. (1996).

McGaugh et al. "Amygdala Role in Modulation of Memory Storage" In the Amygdala: A Functional Analysis, J.P. Aggleton, ed. London: Oxford University Press 391-423 (2000).

Morelli et al. "Induction of Fos-Like-Immunoreactivity in the Central Extended Amygdala by Antidepressant Drugs". Synapse 31:1-4. (1999).

Morris et al. "A Differential Neural Response in the Human Amygdala to Fearful and Happy Facial Expressions" Nature 383:812-815. (1996).

Nozaki et al. "Insight Into the Neuronal Mechanism of Secretin Therapy in Autistic Children" (Abstract) In: IMFAR. Orlando, FL. (2002).

Nozaki et al. "In Vitro Autoradiographic Localization of (125)I-Secretin Receptor Binding Sites in Rat Brain" Biochem. Biophys. Res. Commun. 292:133-137. (2002).

Phillips. "A Specific Neural Substrate for Perceiving Facial Expressions of Disgust". Nature 389:495-498 (1997).

Roberts et al. "Repeated Doses of Porcine Secretin in the Treatment of Autism: A Randomized, Placebo-Controlled Trial" Pediatrics 107:71. (2001).

Rohan et al. "Match-Warped EPI Anatomic Images and the Amygdala: Imaging in Hard Places" (Abstract) In: Proccedings International Society for Magnetic Resonance in Medicine, p. 1237. (2001).

Rosenkranz and Grace. (2001) "Dopamine Attenuates Prefrontal Cortical Suppression of Sensory Inputs to the Basolateral Amygdala of Rats" J Neurosci 21:4090-4103.

Roskoski et al. "Regulation of Tyrosine Hydroxylase Activity in Rat PC12 Cells by Neuropeptides of the Secretin Family" Mol. Pharmacol. 36:925-931. (1989).

Sandler et al. "Lack of Benefit of a Single Dose of Synthetic Human Secretin in the Treatment of Autism and Pervasive Developmental Disorder" N. Engl. J. Med. 341:1801-1806. (1999).

Sanders et al. "Priming of Experimental Anxiety by Repeated Subthreshhold GABA Blockade in the Rat Amygdala" Brain Research 699:250-259. (1995).

Sheline et al. "Increased Amygdala Response to Masked Emotional Faces in Depressed Subjects Resolves With Antidepressant Treatment: An fMRI Study" Biol. Psychiatry 50:651-658. (2001).

Siegle et al. "Can't Shake That Feeling: Event-Related fMRI Assessment of Sustained Amygdala Activity in Response to Emotional Information in Depressed Individuals" Biol Psychiatry 51:693-707. (2002).

Tessitore et al. "Dopamine Modulates the Response of the Human Amygdala: A Study in Parkinson's Disease" J. Neurosci. 22:9099-9103. (2002).

U.S. Congress, Office of Technology Assessment, Biological Components of Substance Abuse and Addiction, Chapter 2:Basic Concepts OTA-BP-BBS-117 (Washington, DC: U.S. Government Printing Office 9-18 (1993).

Yung et al. "Secretin Facilitates GABA Transmission in the Cerebellum" J. Neurosci. 21:7063-7068. (2001).

Yurgelun-Todd et al. "fMRI During Affect Discrimination in Bipolar Affective Disorder" Bipolar Disord. 2:237-248. (2000).

Alamy et al., "Secretin in a Patient with Treatment-Resistant Schizophrenia and Prominent Autistic Features," Schizophr Res. 66(2-3):183-186, 2004.

Blumberg et al., "Amygdala and Hippocampal Volumes in Adolescents and Adults with Bipolar Disorder," *Arch. Gen. Psychiatry* 60(12)1201-1208, 2003.

Blumberg et al., "Frontostriatal Abnormalities in Adolescents with Bipolar Disorder: Preliminary Observations from Functional MRI," *Am. J. Psychiatry* 160(7):1345-1347, 2003.

Blumberg et al., "A Functional Magnetic Resonance Imaging Study of Bipolar Disorder: State- and Trait-Related Dysfunction in Ventral Prefrontal Cortices," *Arch. Gen. Psychiatry* 60(6):601-609, 2003.

Coffman et al., "Cognitive Impairment and Cerebral Structure by MRI in Bipolar Disorder," *Biol. Psychiatry* 27(11):1188-1196, 1990.

Drevets et al., "Functional Anatomical Correlates of Antidepressant Drug Treatment Assessed Using PET Measures of Regional Glucose Metabolism," *Eur. Neuropsychopharmacol.* 12(6):527-544, 2002.

Drevets et al., "Glucose Metabolism in the Amygdala in Depression: Relationship to Diagnostic Subtype and Plasma Cortisol Levels," *Pharmacol. Biochem. Behav.* 71(3):431-447, 2002.

Frangou et al., "The Maudsley Bipolar Disorder Project: Executive Dysfunction in Bipolar Disorder I and its Clinical Correlates," *Biol. Psychiatry* 58(11):859-864, 2005.

Gruber et al., "Decreased Activation of the Anterior Cingulate in Bipolar Patients: an fMRI Study," *J. Affect. Disord.* 82(2):191-201, 2004.

Joseph, "Frontal Lobe Psychopathology: Mania, Depression, Confabulation, Catatonia, Perseveration, Obsessive Compulsions, and Schizophrenia," *Psychiatry* 62(2):138-172, 1999.

Krystal et al., "Glutamate and GABA Systems as Targets for Novel Antidepressant and Mood-Stabilizing Treatments," *Mol. Psychiatry* 7 Suppl 1:S71-80, 2002.

Kuntz et al., "Effects of Secretin on Extracellular Amino Acid Concentrations in Rat Hippocampus," *J. Neural. Transm.* 111(7):931-939, 2004.

Lawrence et al., "Subcortical and Ventral Prefrontal Cortical Neural Responses to Facial Expressions Distinguish Patients with Bipolar Disorder and Major Depression," *Biol. Psychiatry* 55(6):578-587, 2004.

Lembke et al., "Impaired Recognition of Facial Emotion in Mania," *Am. J. Psychiatry* 159(2):302-304, 2002.

Muzina et al., "Maintenance Therapies in Bipolar Disorder: Focus on Randomized Controlled Trials," *Aust. N. Z. J. Psychiatry* 39(8):652-661, 2005.

Myers et al., "Inhibition of Fear Potentiated Startle in Rats Following Peripheral Administration of Secretin," *Psychopharmacology (Berl)* 172(1):94-99, 2004.

Myers et al., "Partial Reversal of Phencyclidine-Induced Impairment of Prepulse Inhibition by Secretin," *Biol. Psychiatry* 58(1):67-73, 2005.

Sheitman et al., "Secretin for Refractory Schizophrenia," *Schizophr. Res.* 66(2-3):177-181, 2004.

Strakowski et al., "A Preliminary fMRI Study of Sustained Attention in Euthymic, Unmedicated Bipolar Disorder," *Neuropsychopharmacology* 29(9):1734-1740, 2004.

Wilder-Willis et al., "Persistent Attentional Dysfunction in Remitted Bipolar Disorder," *Bipolar Disord.* 3(2):58-62, 2001.

Anonymous. "Repligen Discovers Site of Brain Activation by Secretin in Animal Studies Repligen and McLean Hospital to Extend Discovery Through Clinical Trial." *Repligen Corporation: Press Release*, Nov. 12, 2001. (2 pages).

Anonymous. "Secretin is Active in a Brain Region Implicated in Autism." *McLean This Week*, Nov. 4, 2002. (1 page).

Chez et al. "Secretin and Autism: A Two-Part Clinical Investigation." *J. Autism Dev. Disord.* 30:87-94. (2000).

Dunn-Geier et al. "Effect of Secretin on Children with Autism: A Randomized Controlled Trial." *Dev. Med. Child Neurol.* 42:796-802. (2000).

Repligen Corporation. "SecreFlo™ (Secretin) for Injection." (2002) (2 pages).

Rioux et al. "Secretin iv Induces Gene Activation and fMRI Changes in the Amygdala; Potential Relationship to Behaviorial Improvements Seen in Treating Autistic Children." American College of Neuropsychopharmacology, Annual Meeting (2002) (abstract, 1 page).

Robinson. "Homeopathic Secretin in Autism: A Clinical Pilot Study." *Br. Homeopath. J.* 90:86-91. (2001).

Strakowski et al. "Brain Magnetic Resonance Imaging of Structural Abnormalities in Bipolar Disorder." *Arch. Gen. Psychiatry*. 56:254-60. (1999).

Yurgelun-Todd et al. "Increased Amygdala fMRI Activation After Secretin Administration." Society of Biological Psychiatry, 58th Annual Convention and Scientific Program. (2003) (abstract, 1 page).

Yurgelun-Todd et al. "Increased Amygdala fMRI Activation After Secretin Administration." *Exp. Clin Psychopharmacol.* 16:191-198. (2008).

* cited by examiner

US 8,524,665 B2

USE OF SECRETIN IN TREATMENTS OF DISORDERS ASSOCIATED WITH THE AMYGDALA

CROSS-REFERENCE TO RELATED APPLICATIONS

This application is the U.S. National Stage of International Application No. PCT/US2004/015282, filed May 13, 2004, which, in turn, claims the benefit of U.S. Application No. 60/470,177, filed May 13, 2003.

BACKGROUND OF THE INVENTION

The invention relates to the field of treatment of neurological and psychological disorders.

Investigations which utilize functional magnetic resonance imaging (fMRI) techniques have begun to map the regions of the brain that are active during learning, memory, and emotional experiences. Of these regions, the amygdala and, the prefrontal cortex have been shown to be particularly important in affective experience and its modulation. The amygdala has consistently emerged as one of the most critical for ascribing emotional significance to stimuli and influencing affective responsiveness and emotional learning (LeDoux, 1996; Davis, 1997). Neuroimaging studies of adults have shown that the amygdala often produces increased activation in response to several types of affective stimuli, and is activated consistently during the perception of fearful facial expressions (Breiter and Rauch, 1996; Morris et al., 1996; Phillips et al., 1997; Baird et al., 1999). fMRI investigations of individuals with affective disorders, schizophrenia (Kosaka et al., 2002), and autism (Baron-Cohen et al., 1999) have shown an abnormal activation of the amygdala in response to facial emotions and other social stimuli.

Neuroimaging research has also shown that the same amygdala regions that are responsive to the affective value of visual stimuli are also sensitive to pharmacologic manipulation. For example, Kalin and colleagues (1997) demonstrated that while viewing positively and negatively valenced stimuli, depressed patients, unlike control subjects, displayed no amygdalar activation in response to positive stimuli during a baseline evaluation (Kalin et al., 1997). However, following treatment with venlafaxine, depressed patients showed a significant increase in activation to the same positive stimuli. In a study by Sheline and colleagues, depressed patients initially showed increased activation in the left amygdala compared to control subjects when viewing masked emotional faces. Following treatment, the depressed patients exhibited decreased activation in the left amygdala compared to baseline, whereas, control subjects demonstrated no difference in activation between the initial and follow up scans (Sheline et al., 2001). In an additional recent study using negatively and positively valenced words as stimuli, Siegle et al. reported that amygdalar activation to negative words in depressed patients extended significantly longer than the activation produced by control subjects (Siegle et al., 2002). Moreover, a recent study by Hariri et al. (2002) reported increased amygdalar responsivity to facial affect in healthy subjects following the administration of dextroamphetamine, a dopaminergic psychostimulant. The authors suggested that this augmentation may be due to either dopamine-mediated enhancement of excitatory input to the amygdala or attenuation of inhibitory prefrontal input (Hariri et al., 2002).

Abnormal amygdalar function is implicated in many disorders, such as bipolar disorder, that are often recalcitrant to treatment or require treatments that have significant side effects. By focusing on normalizing amygdalar function, it may be possible to treat a variety of conditions with only one therapeutic agent or combination of therapeutic agents. Accordingly, there is a need for novel therapeutic agents to treat disorders associated with the amygdala.

SUMMARY OF THE INVENTION

In general, the present invention provides methods for treating disorders associated with the amygdala. The methods of treatment are based on the administration of a therapeutically effective amount of secretin to an individual suffering from a disorder associated with the amygdala, e.g., bipolar disorder or a substance use disorder.

Accordingly, the invention features a method for treating an individual suffering from a disorder associated with the amygdala by administering a therapeutically effective amount of secretin to the individual. The therapeutically effective amount is, for example, 2 clinical units of secretin per kilogram of bodyweight, and the secretin is administered, for example, by an intravenous, bolus infusion.

In addition, the methods of the invention may include a step of diagnosing a subject with a disorder associated with the amygdala, e.g., bipolar disorder, prior to administration of secretin. The administration may also occur while the patient is receiving continuing treatment by a medical professional.

Exemplary disorders associated with the amygdala include bipolar disorder, anxiety disorders, panic disorder, obsessive-compulsive disorder (OCD), post-traumatic stress disorder (PTSD), phobias, generalized anxiety disorder (GAD), schizophrenia, ADHD, depression, a substance use disorder, and cyclothymia. Preferred disorders for treatment by the methods of the invention include bipolar disorder, panic disorder, post-traumatic stress disorder (PTSD), phobias, generalized anxiety disorder (GAD), a substance use disorder, and cyclothymia.

The method may further include administering an antidepressant, anticonvulsant, antianxiety, antimanic, antipsychotic, antiobsessional, sedative-hypnotic, stimulant, or anti-hypertensive medication. Exemplary antidepressant, anticonvulsant, antianxiety, antimanic, antipsychotic, antiobsessional, sedative-hypnotic, stimulant, or anti-hypertensive medications include alprazolam, buspirone hydrochloride, chlordiazepoxide, chlordiazepoxide hydrochloride, clorazepate dipotassium, desipramine hydrochloride, diazepam, halazepam, hydroxyzine hydrochloride, hydroxyzine pamoate, lorazepam, meprobamate, oxazepam, prazepam, prochlorperazine maleate, prochlorperazine, prochlorperazine edisylate, trimipramine maleate, amobarbital, amobarbital sodium, carbamazepine, chlordiazepoxide, chlordiazepoxide hydrochloride, clorazepate dipotassium, diazepam, divalproex sodium, ethosuximide, ethotoin, gabapentin, lamotrigine, magnesium sulfate, mephenyloin, mephobarbital, methsuximide, paramethadione, pentobarbital sodium, phenacemide, phenobarbital, phenobarbital sodium, phensuximide, phenyloin, phenyloin sodium, primidone, secobarbital sodium, trimethadione, valproic acid, clonazepam, amitriptyline hydrochloride, amoxapine, bupropion hydrochloride, clomipramine hydrochloride, desipramine hydrochloride, doxepin hydrochloride, fluoxetine, fluvoxamine, imipramine hydrochloride, imipramine pamoate, isocarboxazid, lamotrigine, maprotoline hydrochloride, nortriptyline hydrochloride, paroxetine hydrochloride, phenelzine sulfate, protriptyline hydrochloride, sertraline hydrochloride, tranylcypromine sulfate, trazodone hydrochloride, trimipramine maleate, venlafaxine hydrochloride, lithium carbonate, lithium citrate, fluvoxamine, clomipramine hydrochloride, acetophenazine maleate, chlorpromazine hydrochloride, chlorprothixene, chlorprothixene hydrochloride, clozapine, fluphenazine decanoate, fluphenazine enathrate, fluphenazine hydrochloride, haloperidol decanoate, haloperidol, haloperidol lactate, loxapine hydrochloride, loxapine succinate, mesoridazine besylate, molindone hydrochloride, perphenazine, pimozide, prochlorperazine maleate, prochlorperazine, prochlorperazine edisylate, promazine hydrochloride, risperidone, thioridazine, thioridazine hydrochloride, thiothixene, thiothixene hydrochloride, trifluoperzine hydrochloride, amobarbital, amobarbital sodium, aprobarbital, butabarbital, chloral hydrate, chlordiazepoxide, chlordiazepoxide hydrochloride, clorazepate dipotassium, diazepam, diphenhydramine, estazolam, ethchlorvynol, flurazepam hydrochloride, glutethimide, hydroxyzine hydrochloride, hydroxyzine pamoate, lorazepam, methotrimeprazine hydrochloride, midazolam hydrochloride, oxazepam, quazepam, secobarbital sodium, temazepam, triazolam, zolpidem tartrate, dextroamphetamine sulfate, methamphetamine hydrochloride, methylphenidate hydrochloride, pemoline, and clonidine.

By a "disorder associated with the amygdala" is meant any disorder that involves abnormal functioning in the amygdala. Exemplary disorders include bipolar disorder, anxiety disorders such as panic disorder, obsessive-compulsive disorder (OCD), post-traumatic stress disorder (PTSD), phobias (e.g., specific phobia and social phobia), and generalized anxiety disorder (GAD), schizophrenia, ADHD, depression, a substance use disorder, and cyclothymia. Preferred disorders associated with the amygdala include bipolar disorder, anxiety disorders such as panic disorder, post-traumatic stress disorder (PTSD), phobias (e.g., specific phobia and social phobia), and generalized anxiety disorder (GAD), a substance use disorder, and cyclothymia. One skilled in the art can diagnose these conditions based on standard diagnostic tools, e.g., the Diagnostic and Statistical Manual of Mental Disorders, 4$^{th}$ ed. (DSM-IV) American Psychiatric Association, 1994. In certain embodiments, autism is excluded from disorders associated with the amygdala.

By "treating" is meant the medical management of a patient with the intent that a cure, stabilization, or amelioration of the symptoms will result. This term includes active treatment, that is, treatment directed specifically toward improvement of the disorder; palliative treatment, that is, treatment designed for the relief of symptoms rather than the curing of the disorder; preventive treatment, that is, treatment directed to prevention of the disorder; and supportive treatment, that is, treatment employed to supplement another specific therapy directed toward the improvement of the disorder. The term "treatment" also includes symptomatic treatment, that is, treatment directed toward constitutional symptoms of the disorder.

By "therapeutically effective amount" is meant an amount of secretin sufficient to produce a healing, curative, stabilizing, or ameliorative effect either in the treatment of a disorder associated with the amygdala, for example, bipolar disorder.

Other features and advantages of the invention will be apparent from the following description and the claims.

DETAILED DESCRIPTION OF THE INVENTION

Figure 1:
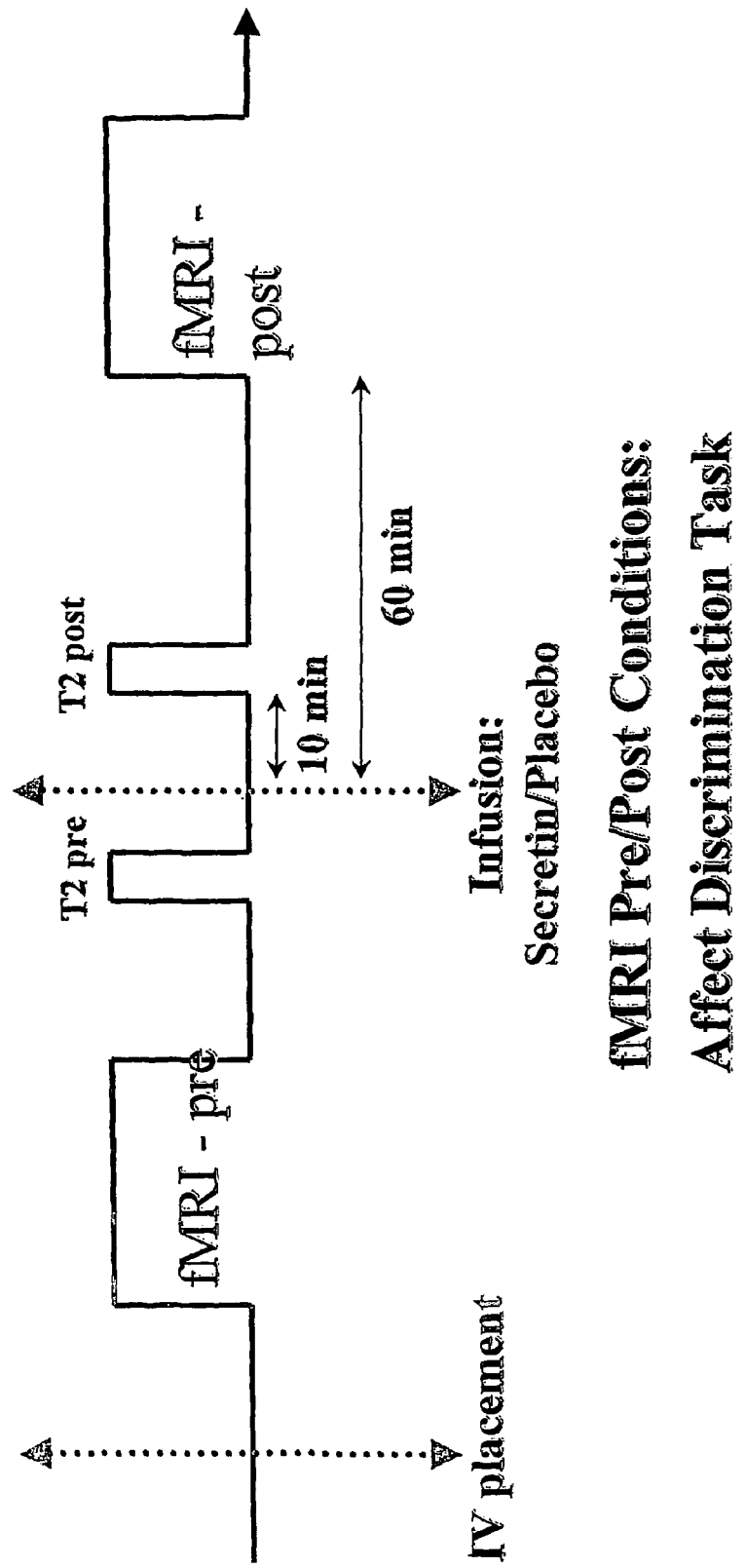
FIG. 1 is a schematic diagram of the fMRI timeline for observation of activity in the amygdala.

The present invention features methods for treating patients suffering from a disorder associated with the amygdala, e.g., bipolar disorder, by administering secretin.

Secretin

Secretin is a polypeptide hormone released when acid chyme enters the intestine. This hormone stimulates the release from the pancreas of fluids that contain bicarbonate and water, which when secreted into the intestine, raise the local pH by neutralizing stomach acid. This change in pH is necessary to increase the efficiency of digestive enzymes. Secretin is FDA approved for use in diagnostic tests for individuals with gastrointestinal disorders.

The methods described herein involve the administration of a therapeutically effective amount of secretin to an individual suffering from a disorder associated with the amygdala. Full-length synthetic human secretin is available from Repligen Corporation (Waltham, Mass.) as RG1068 or SecreFlo™. Alternatively, secretin may be synthesized using synthetic or recombinant methods known in the art. The secretin may, for example, be human (GenBank accession number S07443; HSDGTFTSELSRLREGARLQRLLQGLV; SEQ ID NO: 1), recombinant human, or porcine (GenBank accession number SEPG; HSDGTFTSELSRLREGARLQRLLQGLV; SEQ ID NO: 2), or may be any secretin fragment or analog that exhibits at least 20%, preferably 30%, 50%, or 60%, and most preferably 70%, 85%, 90%, or even 95% of the activity of full-length, wild-type human secretin.

Secretin may be administered by any appropriate route for treatment, stabilization, or prevention of a disorder associated with the amygdala. Secretin may be administered to humans with a pharmaceutically acceptable diluent, carrier, or excipient, in unit dosage form. Administration may be oral, topical, transdermal, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or by any other suitable route of administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in *Remington: The Science and Practice of Pharmacy* (20th ed., A. R. Gennaro ed., Lippincott: Philadelphia, 2000). Formulations for parenteral administration may, for example, contain excipients, sterile water, saline, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, and liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

Secretin may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid, phosphoric acid, or the like. Metal complexes include zinc, iron, and the like.

Conventional pharmaceutical practice may be employed to provide suitable formulations or compositions to administer secretin to patients suffering from a disorder associated with the amygdala. Administration may begin before, during, or after the patient is symptomatic.

The formulations can be administered to human patients in therapeutically effective amounts to provide therapy for a disorder associated with the amygdala, e.g., bipolar disorder. A typical dose for administration in the methods described herein is 2 clinical units (CU)/kg of body weight. For Secre-Flo™, 1 CU is equivalent to 0.2 µg. The clinical unit is as defined by Jorpes et al. (1966). The dose may, however, range, for example, from about 0.05 µg/kg to about 20 µg/kg of body weight per administration, e.g., at least 0.1, 0.2, 0.5, 1, 5, 10, or 15 µg/kg or at most 0.1, 0.2, 0.5, 1, 5, 10, or 15 µg/kg. The exemplary dosage of secretin to be administered is likely to depend on such variables as the type and extent of the disorder, the overall health status of the particular patient, the formulation of the compound, and its route of administration. Standard clinical trials may be used to optimize the dose and dosing frequency for secretin for a particular disorder.

Secretin may be administered as the primary drug or as an adjunct to standard therapy. Standard therapies for disorders associated with the amygdala are known in the art. Preferably, the compounds of the invention, may be administered in conjunction with lower doses of current treatments for these disorders, including stimulants and antidepressants. For example, the compounds of the invention may be administered with phospholipids, e.g., lecithin, or with brain phospholipid precursors, e.g., fatty acids or lipids, or may be administered as an adjunct to standard therapy for the treatment of bipolar disorder or substance use disorders.

Secretin may also be administered in combination with an antidepressant, anticonvulsant, antianxiety, antimanic, antipsychotic, antiobsessional, sedative-hypnotic, stimulant, or anti-hypertensive medication. Examples of these medications include, but are not limited to, the antianxiety medications, alprazolam, buspirone hydrochloride, chlordiazepoxide, chlordiazepoxide hydrochloride, clorazepate dipotassium, desipramine hydrochloride, diazepam, halazepam, hydroxyzine hydrochloride, hydroxyzine pamoate, lorazepam, meprobamate, oxazepam, prazepam, prochlorperazine maleate, prochlorperazine, prochlorperazine edisylate, and trimipramine maleate; the anticonvulsants, amobarbital, amobarbital sodium, carbamazepine, chlordiazepoxide, chlordiazepoxide hydrochloride, clorazepate dipotassium, diazepam, divalproex sodium, ethosuximide, ethotoin, gabapentin, lamotrigine, magnesium sulfate, mephenyloin, mephobarbital, methsuximide, paramethadione, pentobarbital sodium, phenacemide, phenobarbital, phenobarbital sodium, phensuximide, phenyloin, phenyloin sodium, primidone, secobarbital sodium, trimethadione, valproic acid, and clonazepam; the antidepressants, amitriptyline hydrochloride, amoxapine, bupropion hydrochloride, clomipramine hydrochloride, desipramine hydrochloride, doxepin hydrochloride, fluoxetine, fluvoxamine, imipramine hydrochloride, imipramine pamoate, isocarboxazid, lamotrigine, maprotoline hydrochloride, nortriptyline hydrochloride, paroxetine hydrochloride, phenelzine sulfate, protriptyline hydrochloride, sertraline hydrochloride, tranylcypromine sulfate, trazodone hydrochloride, trimipramine maleate, and venlafaxine hydrochloride; the antimanic medications, lithium carbonate and lithium citrate; the antiobsessional medications, fluvoxamine, and clomipramine hydrochloride; the antipsychotic medications, acetophenazine maleate, chlorpromazine hydrochloride, chlorprothixene, chlorprothixene hydrochloride, clozapine, fluphenazine decanoate, fluphenazine enathrate, fluphenazine hydrochloride, haloperidol decanoate, haloperidol, haloperidol lactate, lithium carbonate, lithium citrate, loxapine hydrochloride, loxapine succinate, mesoridazine besylate, molindone hydrochloride, perphenazine, pimozide, prochlorperazine maleate, prochlorperazine, prochlorperazine edisylate, promazine hydrochloride, risperidone, thioridazine, thioridazine hydrochloride, thiothixene, thiothixene hydrochloride, and trifluoperzine hydrochloride; the sedative-hypnotic medications, amobarbital, amobarbital sodium, aprobarbital, butabarbital, chloral hydrate, chlordiazepoxide, chlordiazepoxide hydrochloride, clorazepate dipotassium, diazepam, diphenhydramine, estazolam, ethchlorvynol, flurazepam hydrochloride, glutethimide, hydroxyzine hydrochloride, hydroxyzine pamoate, lorazepam, methotrimeprazine hydrochloride, midazolam hydrochloride, non prescription, oxazepam, pentobarbital sodium, phenobarbital, phenobarbital sodium, quazepam, secobarbital sodium, temazepam, triazolam, and zolpidem tartrate; the stimulants, dextroamphetamine sulfate, methamphetamine hydrochloride, methylphenidate hydrochloride, and pemoline; and the anti-hypertensive, clonidine. Dosages of these compounds are known in the art, e.g., as provided in the *Merck Manual of Diagnosis & Therapy* (17th Ed. M H Beers et al., Merck & Co.) and *Physicians' Desk Reference* 2003 (57th Ed. Medical Economics Staff et al., Medical Economics Co., 2002).

Disorders Associated with the Amygdala

The amygdala is associated with myriad neurological and psychological disorders, such as bipolar disorder, anxiety disorders such as panic disorder, obsessive-compulsive disorder (OCD), post-traumatic stress disorder (PTSD), phobias (e.g., specific phobia and social phobia), and generalized anxiety disorder (GAD), schizophrenia, ADHD, depression, substance use, and cyclothymia. Preferred disorders associated with the amygdala include bipolar disorder, anxiety disorders such as panic disorder, post-traumatic stress disorder (PTSD), phobias (e.g., specific phobia and social phobia), and generalized anxiety disorder (GAD), a substance use disorder, and cyclothymia.

An exemplary disorder associated with the amygdala is bipolar disorder. Bipolar disorder is characterized by changes in mood between manic, major depressive, mixed, and hypomanic episodes. The disorder may also be associated with impairment of work-related, social, or personal functioning Individuals suffering from bipolar disorder may exhibit inappropriate emotional responses and poor judgment compared to healthy individuals and may also exhibit altered responses to emotional stimuli.

Another example of a disorder associated with the amygdala is substance use disorder, e.g., abuse of or dependence on a substance, such as alcohol, opiates, morphine, cocaine, or heroin. Substance abuse is the excessive use of a substance, particularly one that may modify body functions, such as alcohol or opiates. Substance dependence is any form of behavior that indicates an altered or reduced ability to make decisions resulting, at least in part, from the use of a substance, e.g., alcohol or opiates. Representative forms of dependency behavior may take the form of antisocial, inappropriate, or illegal behavior and include those behaviors directed at the desire, planning, acquiring, and use of the substance. This term also includes the psychic craving for the substance that may or may not be accompanied by a physiological dependency, as well as a state in which there is a compulsion to take the substance, either continuously or periodically, in order to experience its psychic effects or to avoid the discomfort of its absence. Forms of dependency include habituation, that is, an emotional or psychological dependence on a substance to obtain relief from tension and emotional discomfort; tolerance, that is, the progressive need for increasing doses to achieve and sustain a desired effect; addiction, that is, physical or physiological dependence which is beyond voluntary control; and use of a substance to prevent withdrawal symptoms. Dependency may be influenced by a number of factors, including physical characteristics of the user (e.g., genetic predisposition, age, gender, or weight), personality, or socioeconomic class.

Imaging of the Effects of Secretin on the Amygdala

To determine the specific neurophysiological effects of secretin on cortical activation, fMRI techniques were applied to healthy control subjects during the viewing of affective faces. Based on our previous findings of increased amygdalar activation in response to viewing fearful facial stimuli, and the preclinical research suggesting that secretin activates amygdala neurons, we hypothesized that following the administration of IV secretin, healthy control subjects would show increased magnitude of BOLD signal change in response to affective stimuli, specifically fearful faces. Our study design included a placebo controlled arm to ensure that measured response change was associated with drug administration and not the result of participation in study procedures. Furthermore, we included three types of affective stimuli (happy, fearful, and neutral) to examine the specificity of amygdalar response.

Methods

Subjects.

Functional neuroimaging data were collected from native English speaking, non-psychiatric subjects, ranging in age from 22 to 34 years (Table 1). All subjects received the Structured Clinical Interview for DSM-IV, Patient edition (Spitzer et al., 1989) to ensure that no history of psychiatric disorder was present, and all subjects had normal or corrected-normal vision. Subjects with a history of head injury, past psychotropic medication use, seizure disorder, substance use or dependence, or neurological disorder were excluded. Additionally, subjects who expressed reticence about entering the magnet environment or who could not complete the scanning protocol because of claustrophobia were removed from the study. All subjects signed an informed consent, which described in detail the scanning procedures and which had been approved by the McLean Hospital Institutional Review Board.

TABLE 1

Subject demographics

| Subject Number | Age | Hand | Education (yrs) | Weight (kg) |
|---|---|---|---|---|
| 1 | 26 | R | 16 | 69.5 |
| 2 | 25 | R | 16 | 78.6 |
| 3 | 24 | R | 16 | 86.8 |
| 4 | 22 | L | 16 | 60.5 |
| 5 | 28 | R | 16 | 73.6 |
| 6 | 24 | L | 16 | 63.6 |
| 7 | 24 | R | 16 | 80.9 |
| 8 | 24 | R | 16 | 62.1 |
| 9 | 30 | R | 18 | 106.1 |
| 10 | 23 | R | 14 | 88.2 |
| 11 | 25 | L | 18 | 114.3 |
| 12 | 34 | L | 13 | 97.5 |
| drug | 24.83 | 2L, 4R | 16.00 | 72.10 |
| placebo | 26.67 | 2L, 4R | 15.83 | 91.52 |
| total average | 25.75 | 4L, 6R | 15.92 | 81.81 |
| t-test (p values) | 0.420 | N/A | 0.85 | 0.07 |

Upon entering the scanner, an N line was started in an antecubital vein and subjects were randomly assigned to receive either placebo (saline) or RG1068 (synthetic human secretin). Drug was administered at 0.4 µg/kg via the N catheter over 1 min. A 3-way stop-clock device with a heparinized line was used to collect blood samples immediately preceding the infusion of RG1068 or placebo and at variable points post infusion for drug pharmacokinetic analysis. Vital signs were monitored for at least 20 minutes after infusion. Prior to the infusion, subjects completed three affective challenge paradigms which had been explained to them before entering the scanner. Subjects completed the same paradigms one hour following infusion with either placebo or RG1068 for pre/post comparison (FIG. 1). This time course was chosen on the basis of previous animal studies which demonstrated significant changes in amygdala gene expression one hour following RG1068 administration (Goulet et al., 2003a).

Stimulation Paradigms.

Three visual activation tasks were presented over separate scanning epochs for all subjects: 1) neutral facial affect, 2) happy facial affect, and 3) fearful facial affect. Prior to the scan, subjects were instructed to view the stimuli and to silently identify the facial expression presented. Stimuli were generated by a Macintosh computer and were projected with a magnetically shielded LCD video projector onto a translucent screen placed at the subjects' feet. The subjects were able to see the screen by the use of a mirror placed above their heads in the scanner. Each scan sequence or epoch was divided into five alternating 30 second segments of rest and activation that lasted for a total of 150 seconds. During baseline and recovery periods, subjects were asked to visually fixate on a white fixation point in the middle of the screen. During activation periods, subjects were required to remain silent and asked to view 3 faces, presented for 9.5 seconds each, in order to determine the facial expression presented. All faces presented were different individuals showing fearful, happy or neutral expressions; no commingling of stimulus type occurred within a scanning epoch; at the conclusion of each scanning epoch, subjects were asked to report the facial affect displayed. Fearful expressions were chosen based on previous work which showed an amygdala related response to fearful faces (Adolphs et al., 1994; Adolphs, 1995). The faces used were black and white photographs taken from Ekman, 1976.

Imaging Methods.

Functional imaging data were acquired on a 1.5 Tesla GE LX MRI scanner equipped with a quadrature RF head coil (TR=3 sec, TE=40 msec, flip angle=90 degrees). Head motion was minimized by comfortable placement of foam padding around the head and a tape strip across the forehead. Functional images were collected from coronal slices which covered the entire brain with a 20 cm field of view and a 64×64 acquisition matrix, with an in-plane resolution of 3.125×3.125×7 mm. Blood Oxygen Level Dependent (BOLD) activation data were collected during the three 50-scan (i.e., 150 sec) runs, each consisting of five alternating 30-second control/task periods. Three dummy images were taken at the outset of each functional scan to reduce non steady-state effects. Matched T1-weighted high-resolution images were also collected for every subject at the beginning of the scanning session.

Image Processing and Analysis.

Functional images were corrected for motion in SPM99 using an intra-run realignment algorithm that uses the first image as a reference. A criterion of 1 mm of head motion in any direction was used as an exclusionary criterion. No subject had motion exceeding this threshold in the present study. BOLD fMRI data were convolved into three-dimensional space and smoothed using an isotropic gaussian kernel (full width half maximum [FWHM]=4 mm). Images were resliced to 2×2×2 mm within Montreal Neurological Institute (MNI) space using sinc interpolation. A statistical parametric map was generated for each subject using the general linear model within SPM99 (Friston et al., 1995a; Friston et al., 1995b) with a hemodynamically corrected box-car waveform employed as the reference paradigm. Multisubject SPMs were created using a fixed effect model to determine the mean suprathreshold activation for the neutral, happy, and fearful affect conditions. The SPM maps were displayed on an average template brain in the standardized coordinate space of the Montreal Neurological Institute within SPM99 (Adolphs et al., 2001). Linear contrasts were then conducted between the post-treatment and pre-treatment conditions to isolate the change in amygdalar activation that was present between treatment groups. To reduce Type I error, the group SPMs and all contrasts were set to an a priori threshold of $p<0.005$, uncorrected, with a minimum cluster-size threshold set at 4 contiguous voxels.

Results

Behavioral Performance Data

All subjects were required to identify the emotion or affect portrayed by the facial stimuli presented during the scanning protocol at the conclusion of each epoch. Although no significant association was found between change in signal intensity data and performance on the facial affect recognition task, it is of note that these normal subjects correctly identified 80-100% of the facial affect presented.

Neuroimaging Data

Baseline Analysis.

Figure 2:
FIGS. 2A-2C are a series of images showing the activation of the amygdala in response to fearful faces.

In order to determine whether or not the presence of an intravenous needle would alter activation significantly in response to the challenge paradigms, we compared two groups of six healthy subjects on the fearful facial activation task; one group had an IV needle attached to a saline drip placed into an antecubital vein, the other had no IV in place. To test the null hypothesis that the mean activation in healthy volunteers with intravenous needle is equal to the mean activation in healthy volunteers without intravenous needle, we used a two-sample t-test (with the significance threshold set at $p=0.001$) on t-contrast images in SPM 99. No significant differences were detected between the IV and no IV groups for amygdalar activation (data not shown). Further comparisons were made to determine whether subjects showed selective responsivity to the valence of the facial stimuli. During the baseline condition, subjects produced significant amygdalar response to fearful faces (FIGS. 2A-2C).

Treatment Effects.

Blood samples were taken over the first 60 minutes post dosing, and samples from subjects receiving RG1068 were used to quantify secretin blood levels. Secretin reached a Cmax (2 min) of 5.1 ng/ml and was eliminated with a half-life (2-20 min) of 3.7 min. Both the Cmax and the elimination rate are consistent with values observed after similar secretin infusions in adults (Christ et al., 1988). Whole brain T2 measures were obtained to verify that no global metabolic effect occurred with the administration of secretin. No significant differences were found between pre/post placebo administration ($p=0.89$) and pre/post secretin administration ($p=0.38$), indicating that secretin has a more region-specific effect on the brain.

Subtraction Analyses.

Figure 3:
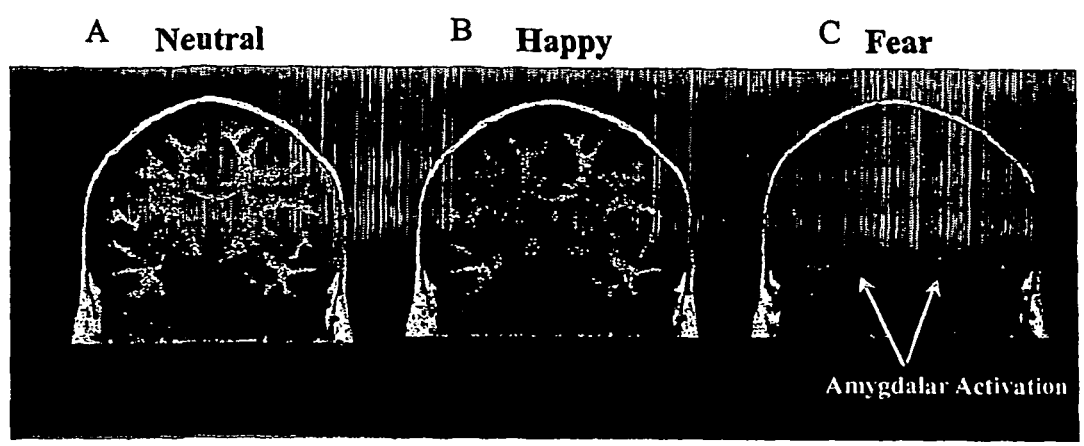
FIGS. 3A-3C are a series of images showing the secretin-induced increase in activation of the amygdala in response to fearful faces.

To determine the patterns of activation produced by each treatment condition relative to the other, the post-drug and pre-drug conditions were subjected to a subtraction analyses in SPM99 and hypotheses regarding the activation of the left and right amygdala were tested using a region of interest (ROI) approach. Anatomic regions were automatically defined using an anatomic MRI atlas (Kinkinis et al., 1996), which we have previously normalized to the same MNI template (Maldjian et al., 1997). MNI coordinates were converted into the Talairach coordinate system (Talairach and Toumoux, 1993) using a non-linear transform (Duncan et al., 2000). Left and right amygala ROIs were determined using the Talairach Daemon (Lancaster et al., 1997; Lancaster et al., 2000). Subtraction of the treatment-baseline activation during the fear condition yielded significant ($p=0.001$) activation in the right amygdala [MNI coordinates: 25, −7, −11] and a non-significant increase in activation in the left amygdala (FIGS. 3A-3C). No significant differences were seen between the treatment conditions for the amygdala when viewing happy or neutral faces.

Discussion

Results from the current investigation examining BOLD changes in response to fearful face stimuli support the hypothesis that secretin alters amygdala responsiveness to affective stimuli. This fMRI observation of a metabolic effect on the amygdala region was not related to task performance, as both groups performed the task equally well, suggesting that these findings are not dependent on labeling of affect or effortful processing. Furthermore, the increased amygdalar activation was not secondary to an N catheterization. Thus, induction of metabolic changes in the amygdala during facial affect processing could be mediated through a variety of signaling pathways.

The dopaminergic system is a prime candidate in this regard since the amygdala receives dopaminergic inputs from both the ventral tegmental area (VTA) and the substantia nigra (SN). In addition, recent fMRI studies have shown that amygdala function is modulated, at least in part, by dopamine (Hariri et al., 2000; Tessitore et al., 2002). In the investigation by Tessitore and colleagues (2002), patients with Parkinson's disease (PD) were studied in a hypodopaminergic state and again during a dopamine replete state while performing a processing task of fearful facial affect. Amygdalar response was potentiated in the dopamine replete state, which the authors suggested may reflect dopamine gating of amygdalar inputs and increased amygdalar neuronal activity (Tessitore et al., 2002). Using an affective challenge paradigm similar to the one of the current study, Hariri and colleagues (2002) reported potentiation of amygdalar response secondary to the administration of dextroamphetamine, a monoamine agonist that works via dopamine transmission (Hariri et al., 2002). Our results are consistent with these imaging studies, as well as preclinical pharmacologic investigations of the amygdala. In one such study which utilized in vivo intracellular recordings in the rat, Rosenkranz and Grace (2001) demonstrated that dopamine potentiated amygdala response by attenuating the inhibitory influence of prefrontal inputs and augmenting the excitatory influence of sensory inputs (Rosenkranz and Grace, 2001). Thus, alterations of the dopaminergic system that lead to increased amygdalar activation may be either inhibitory or excitatory; specifically, excitatory effects may occur in response to direct dopamine related innervation of the amygdala, whereas, inhibition of prefrontal cortical regions would also result in increased amygdala response.

Taken together, these complementary human and animal findings suggest that one possible mechanism by which secretin may modulate affective processing is through alteration(s) of the dopaminergic neurotransmitter system. Tyrosine hydroxlyase (TH), a key enzyme for dopamine synthesis, has been shown to be increased secondary to the administration of secretin. Roskoski et al. (1989) reported a 2 to 3 fold increase in TH concentration in PC12 cells of the rat following the administration of either secretin or vasoactive intestinal polypeptide (VIP); secretin was found to be three times more potent than VIP (Roskoski et al., 1989). Studies of secretin receptor localization in rats have reported peptide binding activity within the nucleus of the solitary tract and laterodorsal thalamic nucleus, as well as the orbital, cingulated, and amygdalar regions (Nozaki et al., 2002a). In a related investigation, Nozaki and colleagues found that the depletion of dopaminergic neurons during the neonatal period in rats resulted in increased secretin binding within the caudate/putamen. Following central administration of secretin, dopamine and its metabolites were shown to be increased within the cerebral cortex, striatum and pons/medulla (Nozaki et al., 2002b).

The interaction of the dopaminergic system with other neurotransmitters, including serotonin, glutamate, and GABA could not be examined with the current study design. However, more than one neurotransmitter system may be affected. For instance, the effects of secretin on amygdalar reactivity in this study may also have been mediated through alterations in GABAergic function. Yung and colleagues have previously reported that administration of secretin selectively facilitates GABAergic neurons within the rat cerebellum (Yung et al., 2001).

Glutamatergic neurons, the main excitatory neurotransmitter in the human brain, originate in multiple brain regions, including the amygdala (Hardingham and Bading, 2003). Previous studies have demonstrated that in rats, blockade of GABAergic function via the injection of a GABAergic antagonist directly into the amygdala results in anxiogenic effects, with behavioral and physiologic characteristics similar to human anxiety states (Saunders et al., 1990). Results from that study indicate that increased activity of amygdalar function with reduced GABAergic inhibition of function produced notable increases in heart rate and blood pressure. Alternatively, it should be noted that GABA agonists like benzodiazapenes can show Fos activation in the central amygdala (Morelli et al., 1999) as was seen with secretin (Goulet et al., 2003a). Taken together, these findings suggest that the administration of secretin selectively increases GABAergic function, which has implications for disorders associated with hypoglutamergic function.

Several factors should be considered in interpreting the study findings. The sample size of each of the study groups consisted of 6 subjects, which limits the generalizability of our findings. With regard to experimental design, the current study utilized a block approach to fMRI techniques as compared to single event fMRI approaches. While the single event technique can provide more precise temporal information regarding response to individual trials, the resultant cortical signal intensity change is small and may not yield sufficient signal to noise in all paradigms (Buckner et al., 1996). Furthermore, interpretation of data still involves averaging responses over multiple stimulus presentations (McKeown et al., 1998). In this study, where the investigation of activation in the amygdala was of primary importance, a block design was used in order to assure the detection of adequate cortical signal.

In human studies, the amygdala has been shown to be a key structure for the regulation of social and emotional responses (Adolphs et al., 1998; Emery and Amaral, 2000). Despite the increased temporal and spatial sensitivity offered by fMRI techniques, mesiotemporal regions, including the amygdala, present special challenges for fMRI studies because of the difficulty in resolving their location and in obtaining signal from these regions (Rohan et al., 2001). However, our group statistical maps indicated significant activation in the amygdala under the fear condition, demonstrating that detectable signal change could be found for some conditions. We interpret the lack of significant amygdalar activation during the happy and neutral conditions as an indication of the reduced stimulus response to these affective challenges; however, it is possible that these reduced activation patterns are related to poor signal due to field inhomogeneities. This observation of secretin effect on BOLD signals in the amygdala may have relevance to observations of secretin activity in autism, a developmental disorder characterized by abnormal amygdala responses to affective stimuli (Howard et al., 2000; Adolphs et al., 2001). In a phase II, study of 126 autistic children receiving three intermittent infusions of secretin over six weeks, a significant improvement in social functioning was observed (Schneider et al., Nov. 1-2, 2002). Impairments in social cognition in autism have been hypothesized to be a manifestation of abnormalities in amygdala function (Baron-Cohen et al., 2000; Howard et al., 2000; Adolphs et al., 2001). Given hypotheses of amygdalar dysfunction in a number of neuropsychiatric diseases, including autism, and the demonstrated effects of secretin on the amygdala, secretin is of potential therapeutic use in disease states that display abnormal amygdala activity.

REFERENCES

Adolphs R, Tranel D, Damasio A R (1998) The human amygdalain social judgement. Nature 193:470-474.

Adolphs R, Sears L, Piven J (2001) Abnormal processing of social information from faces in autism. J Cog Neurosci 13:232-240.

Adolphs R, Tranel D, Damasio H, Damasio A (1994) Impaired recognition of emotion in facial expression following bilateral damage to the human amygdala. Nature 372:669-672.

Adolphs R, Tranel, D., Damasio, H., & Damasio, A. R. (1995) Fear and the human amygdala. J Neurosci 15:5879-5891.

Baird A A, Gruber S A, Fein D A, Maas L C, Steingard R J, Renshaw P F, Cohen B M, Yurgelun-Todd D A (1999) Functional magnetic resonance imaging of facial affect recognition in children and adolescents. J Am Acad Child Adolesc Psychiatry 38:195-199.

Baron-Cohen S, Ring H A, Bullmore E T, Wheelwright S, Ashwin C, Williams S C (2000) The amygdala theory of autism. Neurosci Biobehav Rev 24:355-364.

Baron-Cohen S, Ring H, Wheelwright S, Bullmore E, Brammer M, Simmons A, Williams S (1999) Social intelligence in the normal and autistic brain: an fMRI study. Eur J Neurosci 11:1891-1898.

Breiter H, Rauch S (1996) Functional MRI and the study of OCD: From symptom provocation to cognitive-behavioral probes of cortico-striatal systems and the amygdala. Neuroimage 4:127-138.

Buckner R L, Bandettini P A, O'Craven K M, Savoy R L, Petersen S E, Raichle M E, Rosen B R (1996) Detection of cortical activation during averaged single trials of a cognitive task using functional magnetic resonance imaging [see comments]. Proc Natl Acad Sci USA 93:14878-14883.

Christ A, Werth B, Hildebrand P, Gyr K, Stalder G A, Beglinger C (1988) Human secretin. Biologic effects and plasma kinetics in humans. Gastroenterology 94:311-316.

Coniglio S, Lewis J, Lang C, Subhani-Siddique R, Weintraub A, Schub H, Holden E (2001) A randomized, double-blind placebo-controlled trial of single-dose intravenous secretin as treatment for children with autism. J Ped 138:649-655.

Davis M (1997) Neurobiology of fear responses: the role of the amygdala. J Neuropsychiatry Clin Neurosci 9:382-402.

Duncan J, Seitz R, Kolodny J, Bor D, Herzog H, Ahmed A, Newell F, Emslie H (2000) A neural basis for general intelligence. Science 289:457-460.

Ekman P (1976) Pictures of facial affect. Palo Alto, Calif.: Consulting Psychologists.

Emery N J, Amaral D G (2000) The role of the amygdala in primate social cognition. In: Cognitive neurosicnece of emotion (Lane R D, Nadel L, eds), pp 156-191. New York.

Friston K, Ashburner J, Poline J, Frith C, Heather J, Frackowiak R (1995a) Spatial registration and normalization of images. Human Brain Mapping 2:165-189.

Friston K, Holmes A, Worsley K, Poline J, Frith C, Frackowiak R (1995b) Statistical parametric maps in functional imaging: A general approach. Human Brain Mapping 2:189-201.

Goulet M, P J S, Ware C, Boismenu R, Rusche J (2003a) A secretin intravenous infusion activates gene expression in the central amygdala of rats. Neuroscience.

Goulet M, Shiromani P J, Ware C M, Strong R A, Boismenu R, Rusche J R (2003b) A secretin i.v. infusion activates gene expression in the central amygdala of rats. Neuroscience 118:881-888.

Hardingham G, Bading H (2003) The Yin and Yang of NMDA receptor signaling. Trends in Neurosciences 26:81-89.

Hariri A, Mattay V, Tessitore A, Fera F, Smith W, Weinberger D (2002) Dextroamphetamine modulates the response of the human amygdala. Neuropsychopharmacology 27:1036-1040.

Hariri A R, Bookheimer S Y, Mazziotta J C (2000) Modulating emotional responses: effects of a neocortical network on the limbic system. NeuroReport 11:43-48.

Horvath K, Stefanatos G, Sokolski K, Wachtel R, Nabor L, Tildon J (1998) Improved social and language skills after secretin administration in patients with autistic spectrum disorders. J Assoc Acad Minor Phys 9:9-15.

Howard M, Cowell P, Bouocher J, Broks P, Mayes A, Farrnat A, Roberts N (2000) Convergent neuroantomical and behavioural evidence of an amygdala hypothesis of autism. NeuroReport 11:2931-2935.

Jorpes E, Mutt V (1966) On the biological assay of secretin. The reference standard. Acta Physiol Scand 66:316-325.

Kalin N H, Davidson R J, Irwin W, Warner G, Orendi J L, Sutton S K, Mock B J, Sorenson J A, Lowe M, Turski P A (1997) Functional magnetic resonance imaging studies of emotional processing in normal and depressed patients: effects of venlafaxine. J Clin Psychiatry 58:32-39.

Kinkinis R, Shenton M, Iosifescu D, McCarley R, Saiviroonpom P, Hokama H, Robtaino A, Metcalf D, Wible C, Portas C, Donnino R, Jolesz F (1996) A digital brain atlas for surgical planning, model driven segmentation and teaching. IEEE Transactions on Visualization and Computer Graphics 2.

Kosaka H, Omori M, Murata T, Iidaka T, Yamada H, Okada T, Takahashi T, Sadato N, Itoh H, Yonekura Y, Wada Y (2002) Differential amygdala response during facial recognition in patients with schizophrenia: an fMRI study. Schizophr Res 57:87-95.

Lancaster J, Summerin J, Rainey L, Freitas C, Fox P (1997) The Talairach Daemon, a database server for Talairach Atlas Labels. Neurolmage 5:S633.

Lancaster J, Woldorff M, Parsons L, Liotti M, Freitas C, Rainey L, al. e (2000) Automated Talairach atlas labels for functional brain mapping. Hum Brain Mapp 10:120-131.

LeDoux J (1996) Emotional networks and motor control: a fearful view. Prog Brain Res 107:437-446.

Maldjian J, Schulder M, Liu W, Mun I, Hirschorn D, Murthy R, Carmel P, Kalnin A (1997) Intraoperative functional MRI using a real-time neurosurgical navigation system. J Computer Assisted Tomography 21:910-912.

McKeown M, Jung T, Makeig S, Brown G, Kindermann S, Lee T, Sejnowski T (1998) Spatially independent activity patterns in functional MRI data during the Stroop color naming task. Proceedings of the National Academy of Science 95:803-810.

Morelli M, Pinna A, Ruiu S, Del Zompo M (1999) Induction of Fos-like-immunoreactivity in the Central Extended Amygdala by Antidepressant Drugs. Synapse 31:1-4.

Morris J S, Frith C D, Perrett D I, Rowland D, Young A W, Calder A J, Dolan R J, Morris-Prather C E (1996) A differential neural response in the human amygdala to fearful and happy facial expressions. Nature 383:812-815.

Nozaki S, Mizuma H, Nishimura N, Kohashi R, Watanabe Y (2002b) Insight into the neuronal mechanism of secretin therapy in autistic children (Abstract). In: IMFAR. Orlando, Fla.

Nozaki S, Nakata R, H M, Nishimura N, Watanabe Y, Kohashi R, Watanabe Y (2002a) In vitro autoradiogrpahic localization of (125)i-secretin receptor binding sites in rat brain. Biochem Biophys Res Commun 292:133-137.

Phillips M L, Young A W, Senior C, Brammer M, Andrew C, Calder A J, Bullmore E T, Perrett D I, Rowland D, Williams S C, Gray J A, David A S (1997) A specific neural substrate for perceiving facial expressions of disgust. American Journal of Clinical Hypnosis 40:118-129.

Roberts W, Weaver L, Brian J, Bryson S, Emelianova S, Griffiths A, MacKinnon B, Yim C, Wolpin J, Koren G (2001) Repeated doses of Porcine secretin in the treatment of autism: A randomized, placebo-controlled trial. Pediatrics 107:E17.

Rohan M, Killgore W, Eskesen J, Renshaw P, Yurgelun-Todd D (2001) Match-warped EPI anatomic images and the amygdala: imaging in hard places (Abstract). In: International Society for Magnetic Resonance in Medicine, p 1237.

Rosenkranz J, Grace A (2001) Dopamine atenuates prefrontal cortical supression of sensory inputs to the basolateral amygdala of rats. J Neurosci 21:4090-4103.

Roskoski R, White L, Kowlton R, Roskoski L (1989) Regulation of tyrosine hydroxylase activity in rat PC12 cells by neuropeptides of the secretin family. Mol Pharmacol 36:925-931.

Sandler A D, Sutton K A, DeWeese J, Girardi M A, Sheppard V, Bodfish J W (1999) Lack of benefit of a single dose of synthetic human secretin in the treatment of autism and pervasive developmental disorder. N Engl J Med 341: 1801-1806.

Saunders S K, Morzoratti S L, Shekhar A (1990) Priming of experimental anxiety by repeated subthreshhold GABA blockade in the rat amygdala. Brain Research 24:91-104.

Schneider C, Melmed R, Horvath K, Chey W Y, Perrault J, Wills K, Hansen R, Tager-Flusberg H, Philips J, Krusch D, Corcoran D, Kirwan J, Medeiros L, Manikam R, Borne S, Goodlin-Jones B, Miller M, Silber G, Voigt R, Rusche J, Jauregui K, Rioux P, Herlihy W (Nov. 1-2, 2002) A multi-dose clinical trial of secretin in young children with autism and gastrointestinal symptoms. In: International Meeting for Autism Research (IMFAR). Orlando, Fla.

Sheline Y I, Barch D M, Donnelly J M, Ollinger J M, Snyder A Z, Mintun M A (2001) Increased amygdala response to masked emotional faces in depressed subjects resolves with antidepressant treatment: an fMRI study. Biol Psychiatry 50:651-658.

Siegle G J, Steinhauer S R, Thase M E, Stenger V A, Carter C S (2002) Can't shake that feeling: event-related fMRI assessment of sustained amygdala activity in response to emotional information in depressed individuals. Biol Psychiatry 51:693-707.

Spitzer R, Williams J, Gibbon M (1989) Structured clinical interview for DSM-III-R(SCID) (Patient and Non-Patient Versions). New York State Psychiatric Inst., Biometrics Res. Dept.

Talairach J, Tournoux P (1993) Referentially oriented cerebral MRI anatomy. New York: Thieme Medical Publishers.

Tessitore A, Hariri A, Fera F, Smith W, Chase T, Hyde T, Weinberger D, Mattay V (2002) Dopamine modulates the response of the human amygdala: A study in Parkinson's disease. J Neuroscie 22:9099-9103.

Yung W H, Leung P S, Ng S S, Zhang J, Chan S C, Chow B K (2001) Secretin facilitates GABA transmission in the cerebellum. J Neurosci 21:7063-7068.

OTHER EMBODIMENTS

Modifications and variations of the described methods of the invention will be apparent to those skilled in the art without departing from the scope and spirit of the invention. Although the invention has been described in connection with specific desirable embodiments, it should be understood that the invention as claimed should not be unduly limited to such specific embodiments. Indeed, various modifications of the described modes for carrying out the invention, which are obvious to those skilled in the art, are intended to be within the scope of the invention.

All publications, patents, and patent applications mentioned in this specification are herein incorporated by reference to the same extent as if each individual publication, patent, or patent application was specifically and individually to be incorporated by reference.

Other embodiments are within the claims.

What is claimed is:

1. A method for ameliorating bipolar disorder in an individual in need thereof, said method comprising administering an amount of secretin sufficient to ameliorate bipolar disorder in said to individual.

2. The method of claim 1, wherein said amount is 2 clinical units of secretin per kilogram of bodyweight of said individual.

3. The method of claim 1, wherein said secretin is administered by an intravenous, bolus infusion.

4. The method of claim 1, further comprising administering to said individual an antidepressant, anticonvulsant, anti-anxiety, antimanic, antipsychotic, antiobsessional, sedative-hypnotic, stimulant, or anti-hypertensive medication.

5. The method of claim 4, wherein said medication is selected from the group consisting of alprazolam, buspirone hydrochloride, chlordiazepoxide, chlordiazepoxide hydrochloride, clorazepate dipotassium, desipramine hydrochloride, diazepam, halazepam, hydroxyzine hydrochloride, hydroxyzine pamoate, lorazepam, meprobamate, oxazepam, prazepam, prochlorperazine maleate, prochlorperazine, prochlorperazine edisylate, trimipramine maleate, amobarbital, amobarbital sodium, carbamazepine, divalproex sodium, ethosuximide, ethotoin, gabapentin, lamotrigine, magnesium sulfate, mephenyloin, mephobarbital, methsuximide, paramethadione, pentobarbital sodium, phenacemide, phenobarbital, phenobarbital sodium, phensuximide, phenyloin, phenyloin sodium, primidone, secobarbital sodium, trimethadione, valproic acid, clonazepam, amitriptyline hydrochloride, amoxapine, bupropion hydrochloride, clomipramine hydrochloride, doxepin hydrochloride, fluoxetine, fluvoxamine, imipramine hydrochloride, imipramine pamoate, isocarboxazid, maprotoline hydrochloride, nortriptyline hydrochloride, paroxetine hydrochloride, phenelzine sulfate, protriptyline hydrochloride, sertraline hydrochloride, tranylcypromine sulfate, trazodone hydrochloride, venlafaxine hydrochloride, lithium carbonate, lithium citrate, acetophenazine maleate, chlorpromazine hydrochloride, chlorprothixene, chlorprothixene hydrochloride, clozapine, fluphenazine decanoate, fluphenazine enathrate, fluphenazine hydrochloride, haloperidol decanoate, haloperidol, haloperidol lactate, loxapine hydrochloride, loxapine succinate, mesoridazine besylate, molindone hydrochloride, perphenazine, pimozide, promazine hydrochloride, risperidone, thioridazine, thioridazine hydrochloride, thiothixene, thiothixene hydrochloride, trifluoperzine hydrochloride, aprobarbital, butabarbital, chloral hydrate, diphenhydramine, estazolam, ethchlorvynol, flurazepam hydrochloride, glutethimide, methotrimeprazine hydrochloride, midazolam hydrochloride, quazepam, temazepam, triazolam, zolpidem tartrate, dextroamphetamine sulfate, methamphetamine hydrochloride, methylphenidate hydrochloride, pemoline, and clonidine.

* * * * *

UNITED STATES PATENT AND TRADEMARK OFFICE
CERTIFICATE OF CORRECTION

PATENT NO. : 8,524,665 B2  Page 1 of 1
APPLICATION NO. : 10/556134
DATED : September 3, 2013
INVENTOR(S) : Yurgelun-Todd et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2,119 days.

Signed and Sealed this
Twenty-first Day of February, 2017

Michelle K. Lee
*Director of the United States Patent and Trademark Office*